United States Patent
Suzuki et al.

(10) Patent No.: US 6,752,629 B2
(45) Date of Patent: Jun. 22, 2004

(54) AIR-DRIVEN DENTAL VIBRATORY INSTRUMENT WITH A REPLACEABLE VIBRATOR MODULE

(75) Inventors: Eiji Suzuki, Tokyo (JP); Yutaka Kadota, Tokyo (JP)

(73) Assignee: Micron Co., Ltd. (JP)

( * ) Notice: Subject to any disclaimer, the term of this patent is extended or adjusted under 35 U.S.C. 154(b) by 151 days.

(21) Appl. No.: 10/058,975

(22) Filed: Jan. 30, 2002

(65) Prior Publication Data

US 2002/0119419 A1 Aug. 29, 2002

(30) Foreign Application Priority Data

Feb. 26, 2001 (JP) .......................................... 2001-050339
Jun. 27, 2001 (JP) .......................................... 2001-194494

(51) Int. Cl.[7] .................................................. A61C 1/07
(52) U.S. Cl. ........................................................ 433/119
(58) Field of Search ................................. 433/117, 118, 433/119, 120

(56) References Cited

U.S. PATENT DOCUMENTS

| 3,444,622 A | * | 5/1969 | Mills et al. ................. 433/100 |
| 3,654,502 A | * | 4/1972 | Carmona et al. ........... 433/119 |
| RE29,687 E | | 7/1978 | Sertich .......................... 32/56 |
| 4,453,919 A | | 6/1984 | Takeshita .................... 433/120 |
| 5,190,456 A | | 3/1993 | Hasegawa ................... 433/120 |
| 5,232,363 A | * | 8/1993 | Meller ......................... 433/117 |
| 5,501,596 A | * | 3/1996 | Bailey ........................... 433/86 |
| 5,915,965 A | * | 6/1999 | Ohlsson et al. ............. 433/118 |

FOREIGN PATENT DOCUMENTS

| JP | 59-25738 | 2/1984 |
| JP | 60-55941 | 4/1985 |

* cited by examiner

Primary Examiner—Todd E. Manahan
(74) Attorney, Agent, or Firm—Lorusso, Loud & Kelly

(57) ABSTRACT

An air-driven dental instrument (10) includes a replaceable vibrator module (16) detachably accommodated in an axial lodgment defined by an elongated outer casing (14) comprised of a frontal cap (22A) and a main body (26A) coupled with each other. When the cap (22A) is coupled, the module (16) is axially positioned against the cap (22A) by a positioning sleeve (90A) and is rotationally locked against the sleeve (90A) by a hexagonal formation (128) engaging into cutouts (136) formed on a housing (134). When the cap (22A) is disconnected from the main body (26A), the module (16) is retained by the housing (134) but is partly exposed therefrom. This permits a user to grip the module to thereby facilitate replacement of the module (16).

21 Claims, 12 Drawing Sheets

AIR-DRIVEN DENTAL VIBRATORY INSTRUMENT WITH A REPLACEABLE VIBRATOR MODULE

BACKGROUND OF THE INVENTION

1. Field of the Invention

The present invention relates to improvements in a hand-held air-driven dental vibratory instrument such as an air-driven dental scaler.

2. Description of the Prior Art

It has been customary to use powered dental vibratory instruments to carry out certain dental treatments such as scaling of teeth and reaming of root canals of teeth.

Typically, a powered dental vibratory instrument includes an elongated outer casing adapted to be held by a hand, a vibrator unit arranged within the casing to serve as a source of vibration, and a dental vibratory tool such as a scaling tip and a root canal reamer detachably connected to the vibrator unit, the dental tool being subjected to vibratory movement in response to vibration generated in the vibrator unit to thereby perform desired dental treatment such as scaling and root canal reaming.

The vibrators which are used in the powered dental vibratory instruments may be grouped into two classes according to the principle of operation; electrical vibrators wherein the vibration is generated by making use of an electric power and air-driven vibrators wherein a compressed air is used as a power source.

The electrical vibrators of the first class are disclosed, for example, in JP-A-59-25738 and JP-A-60-55941. An electrical vibrator includes an electrostrictive or piezoelectric transducer which generates vibration in response to application of an alternating voltage. The advantage of the electrical vibrators is that they are substantially free from emission of audible noise because they are operable at a supersonic frequency exceeding 20,000 Hz.

However, the problem involved in the electrical vibrators is that there is a danger that electromagnetic waves emitted from the electrostrictive or piezoelectric transducer would inadvertently cause malfunction of medical electronic and electrical devices and instruments such as a cardiac pacemaker.

In contrast, the air-driven vibrators of the other class are designed to generate vibration in response to oscillatory movement of a rotor or a vibratory element caused by a jet of compressed air supplied from a dental unit. Accordingly, dental instruments incorporating the air-driven vibrators have an advantage that they are free from the problem associated with the emission of the electromagnetic waves.

However, two fundamental problems must be overcome in designing dental instruments equipped with the air-driven vibrators.

The first problem is that a movable part such as a rotor and a vibratory element inevitably undergoes a wear as it is operated. This necessitates replacement of the rotor or vibratory element at the end of its service life. To this end, maintenance must be carried out either by dentists at individual dental clinics or by specialized mechanicians at predetermined repair centers.

The second problem is that, as normally the rotor or vibratory element of the air-driven vibrator could be oscillated only at a frequency in the subsonic or audible range, a very annoying audible sound or noise is generated which often cause a patient uneasy.

To discuss the prior art, U.S. Re. 29,687 (Sertich) discloses 30 a dental scaler incorporating an air-driven vibrator.

The vibrator includes a tubular shaft resiliently supported within an outer casing and a sleeve-like rotor loosely and rotatably mounted over the shaft. Upon injecting compressed air in the tangential direction toward the inner periphery of the rotor through air nozzles formed across the wall of the shaft, the rotor is rotated about the shaft and imparts a vibration thereto. through air nozzles formed across the wall of the shaft, the rotor is rotated about the shaft and imparts a vibration thereto.

The dental scaler of Sertich enjoys the aforementioned advantage of the air-driven vibrator that it is free from the problem caused by the emission of electromagnetic waves.

Furthermore, as the rotor is mounted freely over the shaft and is axially confined by a pair of spaced O-rings fitted over the shaft, the rotor may be readily replaced whenever the rotor is worn out or damaged, by simply removing the shaft out of the outer casing and by removing the positioning O-rings. As in this manner the replacement of the rotor can be readily carried out even by the user, there is no problem of maintenance.

However, the problem of this scaler is that the air-driven vibrator incorporated therein is only able to produce a vibration having a frequency in the range of as low as 3,000–6,000 Hz. This is because vibration takes place in the so-called bending or flexural vibration mode wherein the elongated shaft is excited by the rotating rotor to oscillate by bending or flexural movement of the shaft. Consequently, this scaler cannot solve the afore-mentioned problem inherent in the air-driven vibrators that an annoying audible noise that would make patients uneasy is generated.

U.S. Pat. No. 4,453,919 (Takeshita) describes an arrangement and principle of operation of different type of air-driven vibrator which may be incorporated in a dental scaler as a source of vibration. This vibrator includes a casing provided with a disc-shaped working chamber (or rotor chamber), a disc-shaped vibratory element (or rotor) movably received in the chamber, and injection nozzles for injecting compressed air tangentially into the working chamber.

As compressed air is injected through the nozzles into the working chamber, the vibratory element is oscillated as it is rotated to strike the side walls of the chamber thereby generating a vibration. The vibration generated in the vibrator is transmitted through a shaft to a scaling tip. It is considered that the vibration transmitted through the shaft to the scaling tip is a combination of a flexural mode of vibration and an acoustic or elastic-wave mode of vibration.

U.S. Pat. No. 5,190,456 (Hasegawa) is directed to improve the dental scaler described in U.S. Pat. No. 4,453,919 (Takeshita) and proposes to increase the frequency of vibration of the vibrator as close as possible to the supersonic range in order to reduce the annoying noise inherent in the conventional air-driven vibrators.

To this end, the shaft is shorted in order to transmit to the scaling tip the acoustic or elastic mode of vibration proportionally more than the flexural mode of vibration and the shaft is supported in such a manner as to avoid the presence of a node of vibration which would give rise to the flexural mode of vibration.

According to the concept of U.S. Pat. No. 5,190,456 (Hasegawa), by reducing the size of the vibratory element (or rotor) as far as possible, the frequency of vibration can be increased to approach to the supersonic range in a manner to avoid emission of annoying noise. For example, with a vibratory element having a diameter of as small as 5 mm, the frequency of vibration will be increased up to about 15,000 Hz so that audible noise is considerably subdued.

However, increasing the frequency of vibration will, in turn, accelerate wear of the vibratory element and side walls.

In addition, the more the size of the vibratory element is reduced in an attempt to increase the frequency of vibration to the degree to approach the supersonic range, the effect of wear produced on the vibratory element will be more dominant and serious and this will also shorten the service life of the element. As a result, it will be necessary to replace the vibratory element and side walls more frequently.

However, in contrast to the scaler described in U.S. RE 29,687 (Sertich) wherein the vibrator rotor may readily be replaced by anyone concerned as mentioned hereinabove, in the case of the scaler described in U.S. Pat. No. 5,190,456 (Hasegawa), it is considerably difficult for an ordinary user (e.g., a dentist) to successfully replace the vibratory element and associated wearable parts.

This is firstly because it is difficult to withdraw the vibrator unit as a whole out of the outer casing because the vibrator unit is installed deeply within the elongated outer casing. A special jig is required to drive the vibrator unit out of and into the outer casing.

The second difficulty is related to the fact that the body of the vibrator is made of a plurality of component parts including a pair of side plates defining the working chamber. Consequently, even if the vibrator unit as a whole is successfully removed from the outer casing, the user must further disassemble the vibrator body into parts in order to gain access to the vibratory element for replacement. A special tool must also be used to disassemble and re-assemble the vibrator body and such work is generally difficult to carry out for an ordinary user.

Thirdly, in the vibrator described in U.S. Pat. No. 5,190, 456, it is important that the vibratory element is well matched in vibration with the side plates in order to effectively generate a high frequency vibration. It has often been experienced that mere replacement of the vibratory element or side plates is not sufficient to restore the output performance of the vibrator.

For these reasons, it has been necessary for the users of the dental scalers described in U.S. Pat. No. 5,190,456 to ship their scalers to remote repair centers or factories in order to have the worn parts or the vibrator unit as a whole replaced by skilled mechanicians. This has caused an inconvenience on the users in that the users are obliged to discontinue the use of their scalers until the scalers are repaired and returned back to the users.

SUMMARY OF THE INVENTION

Accordingly, an object of the present invention is to provide an air-driven dental vibratory instrument, including a dental scaler, which permits a user to readily replace the vibrator unit as a whole whenever replacement of a vibratory element and/or associated parts is necessary and which, therefore, is user-friendly to the effect that the user is ensured uninterrupted continued use of the instrument.

Another object of the invention is to provide an air-driven dental vibratory instrument which is so designed as to encourage the user to carry out self-maintenance and to replace a vibrator unit as a whole whenever replacement of the vibratory element and/or associated parts is necessary.

This invention provides an air-driven dental vibratory instrument, comprising, an elongated outer casing having a longitudinally extending lodgment defined contiguous to a frontal end of the casing, said casing being split into a main body and a frontal cap which are detachably coupled with each other by means, for example, of threaded coupling, an air-driven vibrator module or unitary assembly replaceably accommodated in said lodgment, said module having a vibratory element for generating vibration, said module having threaded coupling means for detachably coupling a vibratory tool to the frontal part of the module, means for resiliently supporting the module in the casing, axial positioning means for locating the vibrator module against the frontal cap, means for supplying compressed air to the vibrator module to excite the vibratory element, and, anti-rotation means for preventing the vibrator module from rotating relative to the casing when the vibratory tool is screwed to and unscrewed from the vibrator module. As used herein, the term "front" and "rear" refer to the direction as seen from an user of the instrument during use.

According to the invention, the axial position of the juncture between the main body and the frontal cap is selected such that, when the main body and the frontal cap are disconnected from each other for replacement of the vibrator module, at least part of the vibrator module is exposed from the main body or frontal cap to which it is attached, to thereby permit an operator to hold the module by fingers in order to remove the module from the main body or frontal cap.

With this arrangement, whenever the user has come to believe that the power output of the air-driven vibrator incorporated in the dental instrument is lowered as a result of wearing of the vibratory element or associated parts, the user may unscrew the threaded coupling of the outer casing to disconnect the main body and the frontal cap from one another. As the main body and the frontal cap are separated, the vibrator module will remain attached to either the main body or the frontal cap, as the case may be, and the frontal or rear part of the vibrator module will be exposed from the main body or frontal cap to which it is attached. This will cause the user to recognize that the vibrator module is designed replaceable and will also visually encourage the user to replace it with a new one by him or herself.

Upon being so encouraged, the user may then remove the module from the main body or frontal cap in a simple manner, by holding the exposed part of the vibrator module by the fingers of the one hand and the main body or frontal cap by the other hand, and by merely pulling the module and the main body (or frontal cap) apart. Upon simply installing a new vibrator module to the main body or frontal cap and by screw coupling the main body and the frontal cap with each other, the dental instrument will be ready for reuse. The used vibrator module may be disposed of or sent to repair center for repair.

In this manner, the vibrator module is replaced as a whole simply by disconnecting the main body and the frontal cap from each other, by gripping a used vibrator module to remove it from the main body or frontal cap, by installing a new vibrator module thereto, and by threadingly connecting the main body and the frontal cap with each other. As all these operations may be carried out by hands without requiring a special tool or jig, replacement of the module may be done quite easily and quickly.

Accordingly, whenever the power of the vibrator is lowered as a result of wear of the vibratory element, for example, the user is able to renew the vibrator module at once, to thereby avoid any loss of time that would otherwise be necessary hitherto to ship the dental instrument for repair and to have the repaired instrument returned.

The users may be furnished with one or more spare vibrator modules which after assemblage are checked and inspected for a predetermined level of performance. Therefore, the replaced module will always develop a desired high level of vibration energy.

In one embodiment of the invention, the anti-rotation mechanism is operable to lock the vibrator module against the frontal cap. This will cause the vibrator module to remain attached to the frontal cap when the main body and the frontal cap are disconnected from each other. The axial length of the frontal cap is made smaller than, preferably roughly equal to a half of, the axial length of the vibrator module. With this arrangement, the rear half of the vibrator module will be exposed from the frontal cap as the main body and the frontal cap are disconnected, to thereby permit the operator to securely and readily grip on the module when removing the module from the frontal cap.

In this embodiment wherein the anti-rotation mechanism locks the vibrator module against the frontal cap, a torque applied to the vibratory tool as it is screwed to and unscrewed from the vibrator module will be withstood by the frontal cap. As a result, there is a risk that the frontal cap is undesirably overtightened against and loosened from the main body, as the vibratory tool is screwed to and unscrewed from the vibrator module.

To avoid such inconvenience, according to a preferred embodiment of the invention, the anti-rotation mechanism is designed to lock the vibrator module against the main body of the outer casing. With this arrangement, a torque applied to the vibratory tool to screw it to or unscrew it from the vibrator module will be withstood by the main body so that the frontal cap is exempt from the torque. This prevents the frontal cap from being inadvertently over-tightened or loosened.

In this embodiment wherein the anti-rotation mechanism locks the vibrator module against the main body, the vibrator module will remain attached to the main body when the main body and the frontal cap are disconnected from each other. The axial length of the frontal cap may be made smaller than, preferably roughly equal to a half of, the axial length of the vibrator module to ensure that the frontal half of the vibrator module is exposed from the main body to facilitate operator's grip when removing the module from the frontal cap.

In another preferred embodiment of the invention, the axial positioning means includes a positioning sleeve extending axially within the casing and secured to the main body and the anti-rotation mechanism is operable to lock the vibrator module against the positioning sleeve to ensure that the vibrator module will remain attached to the positioning sleeve when the frontal cap is disconnected from the main body. Furthermore, the juncture between the main body and the frontal cap is located rearwardly of the frontal end of the positioning sleeve to ensure that a frontal part of the vibrator module is exposed from the positioning sleeve as the main body and the frontal cap are disconnected from each other.

As in this embodiment the juncture between the main body and the frontal cap is shifted rearwardly of the anti-rotation mechanism, the frontal cap may be rendered slim at a location at which the operator's fingers are engaged during use of the dental instrument. This improves the operator's grip and facilitates to precisely position the instrument during dental treatment.

Preferably, the axial length of the frontal cap is made greater than a half of the entire axial length of the outer casing and, more preferably, the frontal cap is made long enough to cover substantially the entire length of the instrument. It will be noted that it is easy to subject the frontal cap as separated from the vibrator module to autoclave sterilization and supersonic cleansing. The dental instrument may be kept more clean and hygienic by increasing the length of the cap in a manner to cover substantially the entire length of the instrument and by frequently sterilizing the frontal cap.

Preferably, the anti-rotation mechanism includes at least one notch formed on the inner periphery of the main body and at least one corresponding projection provided on the outer periphery of the vibrator module for engagement with the notch. With this arrangement, the vibrator module may readily be fitted within the lodgment provided in the frontal cap or main body. Preferably, a formation of a polygonal cross-section, more preferably hexagonal cross-section, is provided on the outer periphery of the vibrator module. This enables the user to fit the module in the frontal cap or main body only after a limited relative angular movement.

These features and advantages of the invention, as well as other features and advantages thereof, will become apparent from the following description.

DESCRIPTION OF THE PREFERRED EMBODIMENTS

Figure 1:
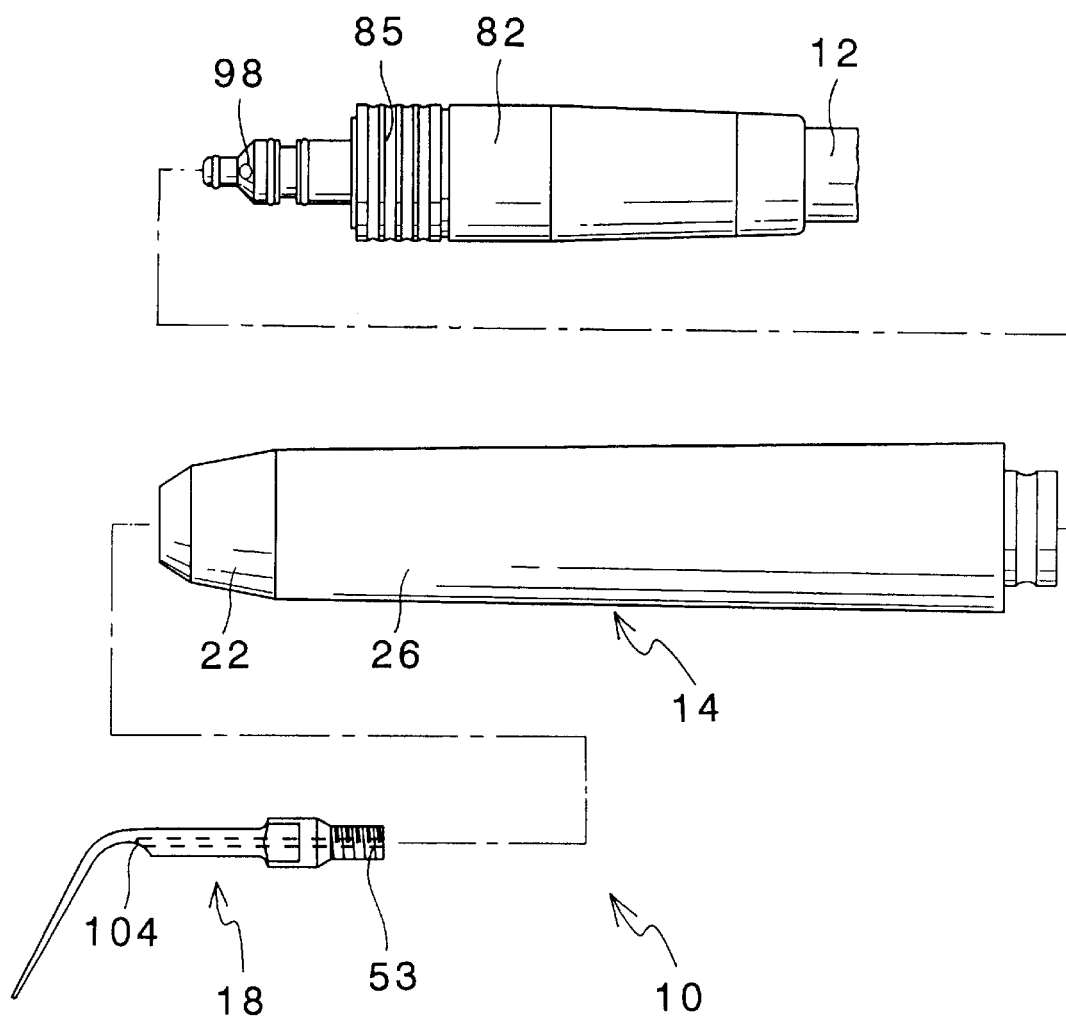
FIG. 1 is an elevational view of the air-driven dental scaler according to the first embodiment of the invention, with the scaling tip and hose coupling disconnected.

In FIGS. 1–6C, there is shown a hand-held air-driven dental scaler according to the first embodiment of the invention.

Referring to these drawings, the dental scaler 10 is designed in the form of a dental handpiece which is adapted to be connected through a dental hose 12 to a dental unit, not shown, so as to be provided with a supply of compressed air and water therefrom.

The dental scaler 10 has a hand-held elongated tubular outer casing 14 in which an air-driven vibrator module or assembly 16 is replaceably accommodated. When the handpiece is used as a dental scaler, a conventional scaling tip 18 as a vibratory tool is detachably mounted to the frontal end of the vibrator module 16. Alternatively, when the handpiece is to be used for reaming of a root canal of a tooth, a conventional reamer or dental file, not shown, may be mounted to the vibrator module or assembly 16 in place of the scaling tip 18.

The outer casing 14 is divided into a short frontal cap 22 provided with an external male thread 20 (FIGS. 3 and 6A) and an elongated main body 26 provided with an internal female thread 24 (FIG. 3), the cap 22 and the main body 26 being threadingly coupled in a detachable fashion to form the outer casing 14.

The frontal cap 22 is provided with a stepped axial bore 27 and the vibrator module 16 is so shaped in its outer configuration that it is fitted partly in the stepped bore 27 with a small clearance.

Figure 2:
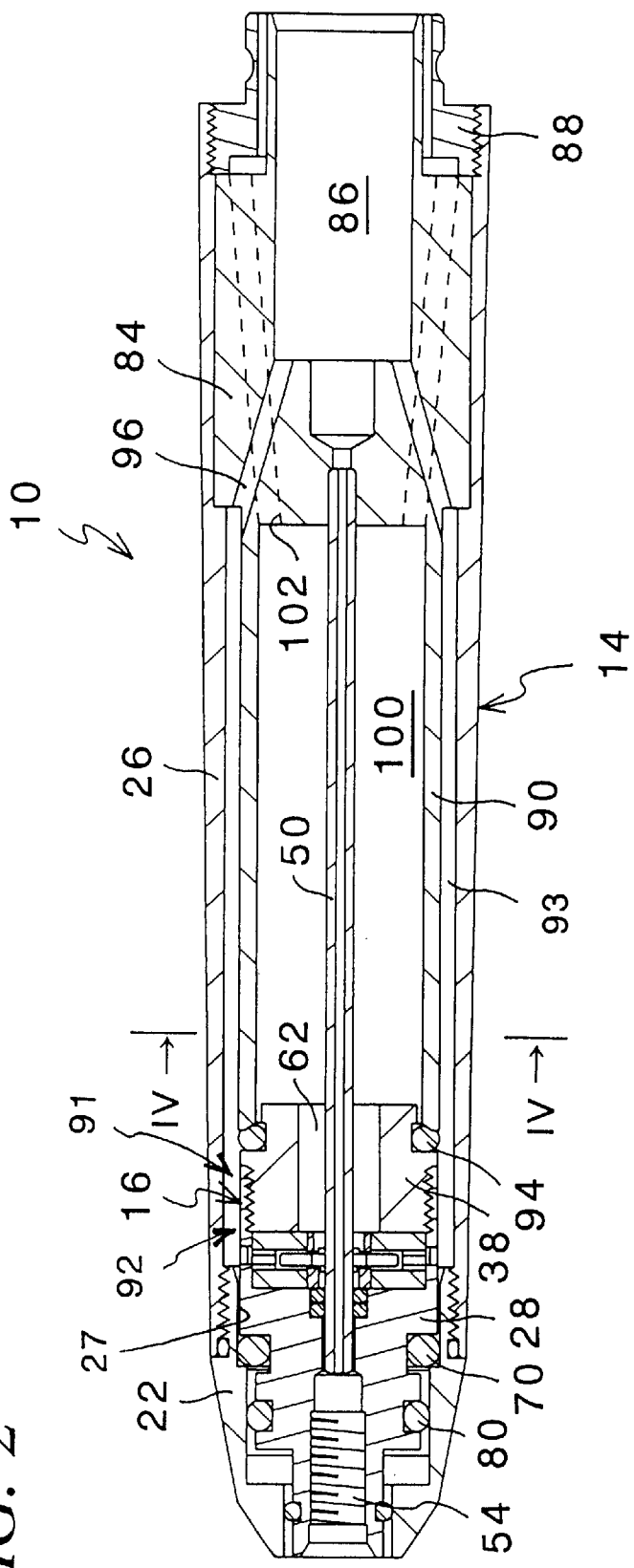
FIG. 2 is a longitudinal cross-sectional view of the scaler shown in FIG. 1.
Figure 6A:
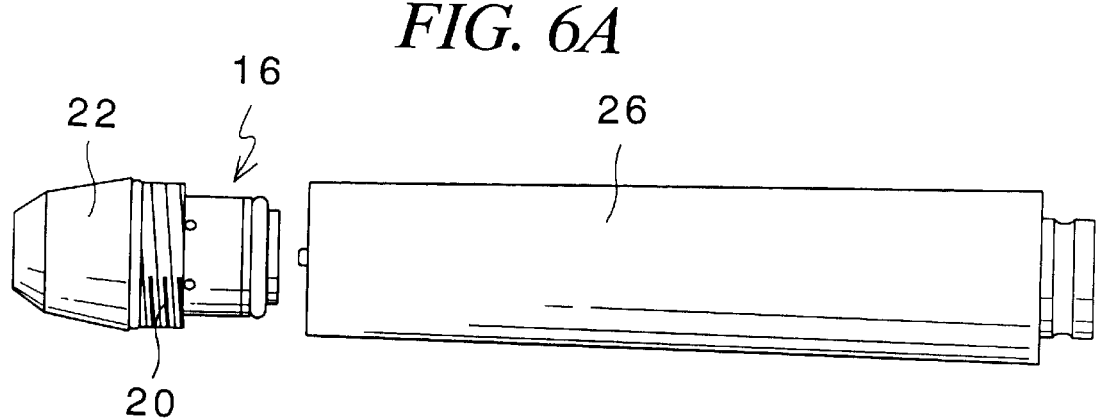
FIGS. 6A–6C illustrate a sequence of procedures for replacing the vibrator module of the scaler shown in FIGS. 1–3.
Figure 6B:
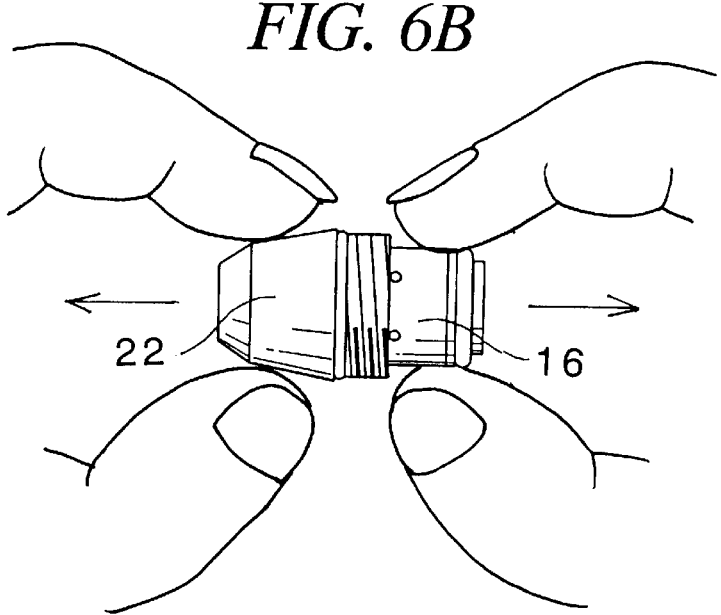

As best shown in FIGS. 2 and 6A, the axial length of the frontal cap 22 is roughly equal to a half of that of the vibrator module 16. Consequently, when the vibrator module 16 is mounted to the frontal cap 22, only the frontal half of the vibrator module 16 will be received within the cap 22 so that the rear half of the module will be exposed from the cap 22, as shown in FIG. 6B.

The vibrator module 16 is in general designed to operate according to the principle of operation described in the aforementioned U.S. Pat. No. 4,453,919 (Takeshita) and is specifically designed similar to that of the vibrator described and shown in U.S. Pat. No. 5,190,456 (Hasegawa). Therefore, the disclosure of these patents is incorporated by reference herein and the principle of operation and the general arrangement of the vibrator module 16 will be described hereafter only briefly.

Figure 3:
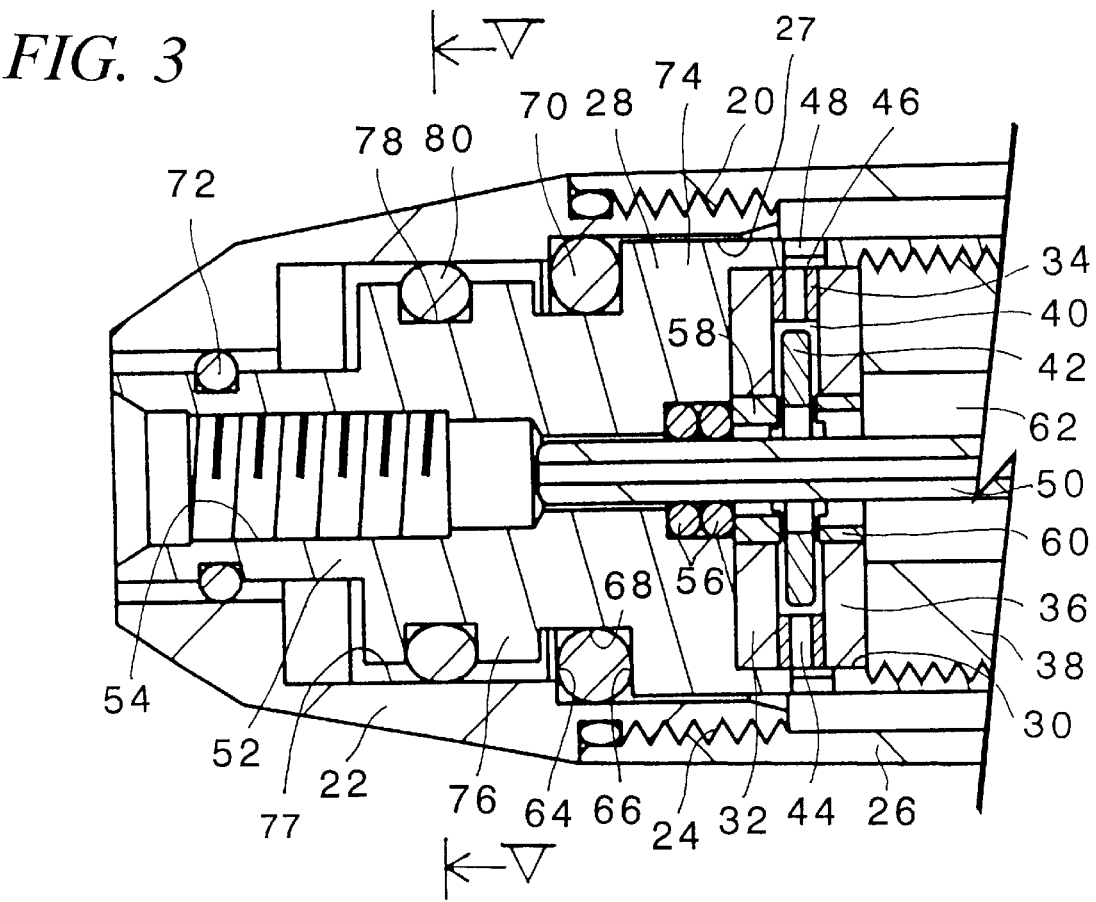
FIG. 3 is an enlarged cross-sectional view of a portion of the scaler shown in FIG. 2.
Figure 4:
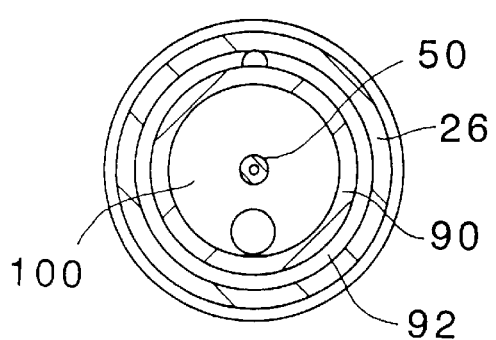
FIG. 4 is a cross-sectional view taken along the line IV—IV of FIG. 2.

As shown enlarged in FIG. 3, the vibrator module 16 includes a metallic casing 28 in the form of a stepped cylinder provided with an axial bore 30 in which a disc-shaped first side plate 32, an air injection ring 34 and a disc-shaped second side plate 36 are mounted in the order mentioned, these members 32, 34 and 36 being held together by a retaining screw 38 screwed into the casing 28.

A disc-shaped working chamber or rotor chamber 40 is defined by the inner faces of the side plates 32 and 36 and by the inner periphery of the air injection ring 34 and a rotor or vibratory element 42 in the form of an apertured disc is received in the chamber 40 for vibratory movement. The outer diameter and the axial thickness of the vibratory element or rotor 42 are selected to be slightly smaller than the inner diameter and the axial size of the working chamber 40, respectively, so as to allow the element 42 to perform a vibratory or oscillatory movement within the working chamber 40.

To enhance the wear resistivity, the side plates 32 and 36 and the rotor 42 are preferably made of a hard alloy such as a high speed steel and are subjected to suitable surface hardening treatment.

It is desirable to make the vibratory element 42 as small in size as possible in order to operate the vibrator at a high frequency of vibration of more than 15,000 Hz which is close to the supersonic range. A preferred axial thickness of the vibratory element or rotor 42 is about 0.4–0.8 mm and a preferred outer diameter thereof is about 5–8 mm.

The vibrator module 16 may be supplied to the users in the form of disposable module or cartridge which cannot be disassembled into parts by the users by loosening the retaining screw 38 in an attempt to replace the element 42.

The air injection ring 34 is provided with a plurality of injection nozzles 44, for example three in number, which are circumferentially equally spaced apart from one another. Although shown only schematically in FIG. 3, these injection nozzles 44 are arranged to open tangentially into the working chamber 40 to ensure that an air jet injected through the nozzles 44 into the chamber 40 produces a strong swirling air stream therein, as described and shown in U.S. Pat. No. 4,453,919 and U.S. Pat. No. 5,190,456.

To supply compressed air to the injection nozzles 44, the casing 28 of the vibrator module 16 is provided along its inner periphery facing the injection nozzles 44 with a circumferentially extending groove 46 which, in turn, is communicated with a plurality of radial air inlet ports 48 (also see FIG. 6C) circumferentially spaced apart from one another. Compressed air is supplied to these inlet ports 48 in a manner described later.

To feed water for cooling and cleaning the scaling tip 18 and teeth during scaling operation, a water supply pipe 50 is arranged to extend through a central opening formed across the casing 28, the side plates 32 and 36, and the retaining screw 38, respectively. The vibratory element 42 is also provided with a central opening to ensure that the vibratory movement of the element is not interfered by the water pipe 50.

The forward end of the water pipe 50 opens into a female threaded bore 54 (FIG. 3) formed in a reduced diameter shank portion 52 of the casing 28 in order to screw mount a male threaded coupling portion 53 (FIG. 1) of the scaling tip 18. The water pipe 50 and the casing 28 are sealed with each other by means of one or more O-rings 56 (FIG. 3).

In order to prevent the vibratory element 42 from undesirably sticking to the inner face of the side plates 32 and 36 when the vibrator is not operated, a pair of bushes 58 and 60 having an axial length slightly greater than the axial thickness of the side plates are press fitted in the central bores of the side plates 32 and 36. The details of the bushes are described in U.S. Pat. No. 5,997,172, the disclosure of which is incorporated by reference herein.

Used air in the working chamber 40 will be exhausted through the inner space of the bush 60 and the central opening 62 of the retaining screw 38, the opening 62 thus serving also as an exhaust port.

As best shown in FIG. 3, the axially extending stepped bore 27 of the cap 22 is provided with a rearwardly directed positioning shoulder 64, and the vibrator casing 28 is correspondingly provided with a positioning shoulder 66 opposing the shoulder 64. An O-ring 70 is mounted in an outer groove 68 formed on the casing 28. The vibrator module 16 will be axially positioned with respect to the cap 22 by urging the module 16 against the cap 22 by means of a positioning sleeve 90, described later in more detail, in such a manner that the O-ring 70 is properly compressed between the shoulders 64 and 66.

The O-ring 70 serves to vibrationally isolate the frontal cap 22 from the vibrator module 16 as well as to air tightly seal the cap 22 and casing 28 with each other. Another O-ring 72 may be used to resiliently support the shank 52 of the casing 28 with respect to the cap 22.

Figure 5:
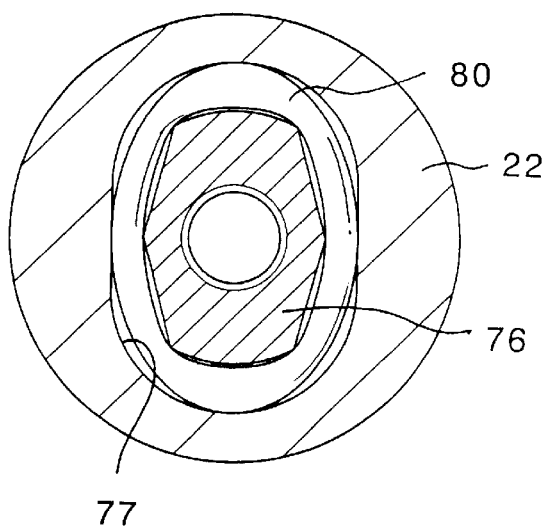
FIG. 5 is a cross-sectional view taken along the line V—V of FIG. 3.

Anti-rotation arrangement must be provided to prevent the vibrator module 16 from undesirably rotating relative to the outer casing 14 when the scaling tip 18 is screwed to and unscrewed from the threaded bore 54 formed in the shank 52 of the casing 28 of the module 16. In the first embodiment, the casing 28 is rotationally locked against the cap 22. To this end, as shown in FIGS. 3 and 5, an intermediate section 76 having an oval cross-section is provided between the shank 52 and an enlarged diameter portion 74 of the casing 28 and the inner periphery 77 of the cap 22 is shaped to present a complementary oval cross-section, to ensure that the sides of the oval section 76 of the vibrator casing 28 are brought into contact with the oval inner periphery 77 of the cap 22 to thereby limit the rotation of the casing 28 relative to the cap 22. An elastomeric O-ring 80 may be mounted in an outer groove 78 of the section 76 to prevent vibration of the module 16 from being transmitted through the section 76 to the cap 22.

Referring to FIGS. 1 and 2, the dental scaler 10 is intended to be connected in a conventional manner to the dental hose 12 extending from a dental unit, not shown. To this end, a first member 82, male member for example, of a conventional hose coupling is attached to an end of the dental hose 12 and a second member 84, female member for example, is provided at the rear end of the main body 26 of the outer casing 14. In the embodiment shown in FIGS. 1 and 2, the first coupling member on the hose 12 is in the form of a plug 82 provided with a conventional ball-lock type quick coupling mechanism 85 and the second coupling member on the outer casing 14 is in the form of a socket 84 having a stepped bore 86 in which the plug 82 is inserted. The socket member 84 is snugly inserted into the main body 26 and is held in position by a retaining screw 88 screwed into the main body 26.

The positioning sleeve 90 may be formed integrally and concentrically with the socket 84 as shown in FIG. 2. The positioning sleeve 90 serves to axially locate the vibrator module 16 against the frontal cap 22. Before threadingly coupling the cap 22 and the main body 26 with each other, the vibrator module 16 is inserted partly into the cap 22, with an O-ring 94 being mounted in an outer groove formed on the retaining screw 38 of the vibrator module 16. Once the cap 22 and the main body 26 are screwed in with each other by the engagement of the screw threads 20 and 24, the positioning sleeve 90 urges and positions the vibrator module 16 against the cap 22, as shown in FIGS. 2 and 3, with the O-ring 70 compressed between the shoulders 64 and 66.

The frontal end of the positioning sleeve 90 is indented rearwardly of the frontal end of the main body 26 of the outer casing 14. Consequently, a forwardly opened cavity 91 is formed within the main body 26 between the frontal end of the main body 26 and the frontal end of the positioning sleeve 90. This cavity 91 cooperates with the stepped axial bore 27 of the cap 22 to form a lodgment 92 for accommodating the vibrator module 16.

An annular space 93 between the positioning sleeve 90 and the casing main body 26 serves as a passage for compressed air. Such arrangement is advantageous in simplifying the structure of the dental scaler 10.

The annular space 93 is, on the one hand, in communication with the plug receptacle bore 86 of the socket 84 through an air passage 96 (FIG. 2) formed in the socket 84 of the hose coupling and will be communicated with an air supply port 98 (FIG. 1) of the plug 82 when the plug 82 of the hose coupling is inserted into the socket 84. The annular space 93, on the other hand, is communicated with the air inlet ports 48 of the vibrator casing 28 so that compressed air is supplied through the inlet ports 48 and through the inner groove 46 of the casing 28 to the injection nozzles 44 of the injection ring 34.

Used air in the working chamber 40 will be returned back to the dental hose 12 through the central opening 62 (FIG. 2) of the retaining screw 38, an annular space 100 between the positioning sleeve 90 and the water pipe 50, and an exhaust passage 102 formed on the socket 84 of the hose coupling.

Cooling and cleaning water may be supplied to the scaling tip 18 through a central water passage, not shown, formed in a conventional manner in the plug 82 of the hose coupling and through the water pipe 50 to a water passage 104 (FIG. 1) formed in the scaling tip 18. The rear end of the water pipe 50 is securely supported by the socket 84.

In use, a wrench is used to firmly screw the scaling tip 18 into the threaded bore 54 of the vibrator module 16 and the plug 82 of the dental hose 12 is inserted into the socket 84 of the hose coupling of the outer casing 14 to supply compressed air to the vibrator. As compressed air is injected through nozzles 44 into the working chamber 40 in the tangential direction, a swirling stream of jet is generated in the chamber 40, causing the vibratory element 42 to oscillate to produce vibration according to the principle described in U.S. Pat. No. 4,453,919. The vibration generated in the vibrator module 16 is transmitted to the scaling tip 18 to vibrate it at a high frequency of vibration close to the supersonic range according to the principle described in U.S. Pat. No. 5,190,456.

As the dental scaler 10 is used, the vibratory element 42 and the side plates 32 and 36 will undergo wear so that the power output of the vibrator 16 will decrease. In that event, the user may readily replace the vibrator module 16 as a whole in the following manner.

First, a suitable wrench is used to unscrew and remove the scaling tip 18 from the vibrator module 16. Then, the user grips the cap 22 and the main body 26 of the outer casing 14 by respective hands and unscrews the cap 22 and the main body 26 from each other until the cap 22 is disconnected from the main body 26 as shown in FIG. 6A.

Because the vibrator module 16 is rotationally locked against the frontal cap 22 by the anti-rotation arrangement 76/77, the water pipe 50 will be pulled out of the O-rings 56 while being rotated relative to the O-rings 56 when the cap 22 and the main body 26 are unscrewed from each other. Therefore, there is a sliding friction at the contact between the water pipe 50 and the O-rings 56. In contrast, at the contact between the cap 22 and the O-rings 70 and 72, there exists a static friction which will overcome the sliding friction exerted between the water pipe 50 and the O-rings 56.

As a result, when the cap 22 and the main body 26 are separated, the vibrator module 16 will remain attached to the frontal cap 22 as shown in FIG. 6A due to the static friction by the O-rings 70 and 72. At this state, a half of the vibrator module 16 will be exposed rearwardly out of the frontal cap 22. This will visually encourage the user to replace the vibrator module 16 with a new one. As the rear half of the vibrator module 16 is exposed, it can be readily gripped by fingers.

Figure 6C:
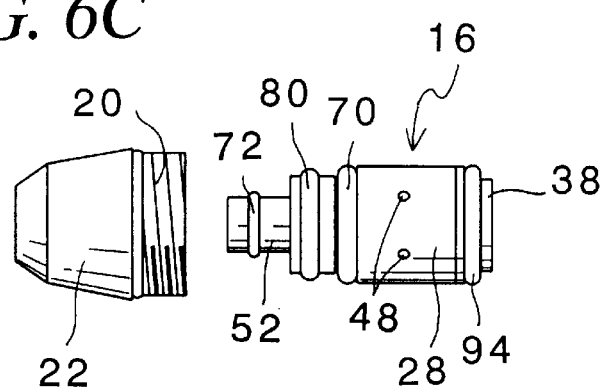

Accordingly, by holding the cap 22 by the fingers of the one hand, with the vibrator module 16 held by the fingers of the other hand, and by pulling the cap and the module apart as shown in FIG. 6B, the vibrator module 16 will be readily separated from the cap 22 as shown in FIG. 6C.

Thereafter, by merely installing a new vibrator module to the cap 22, and upon screw coupling the cap 22 and the main body 26 with each other, the dental scaler 10 will again be in a condition for use once the scaling tip 18 is mounted.

In this manner, according to the invention, whenever a loss of power of the vibrator due to wear of the vibratory element and associated parts is sensed, the vibrator module may readily be replaced by anyone without resort to any special jig or tool. The used vibrator module may be disposed of or sent to a repair center.

Figure 7:
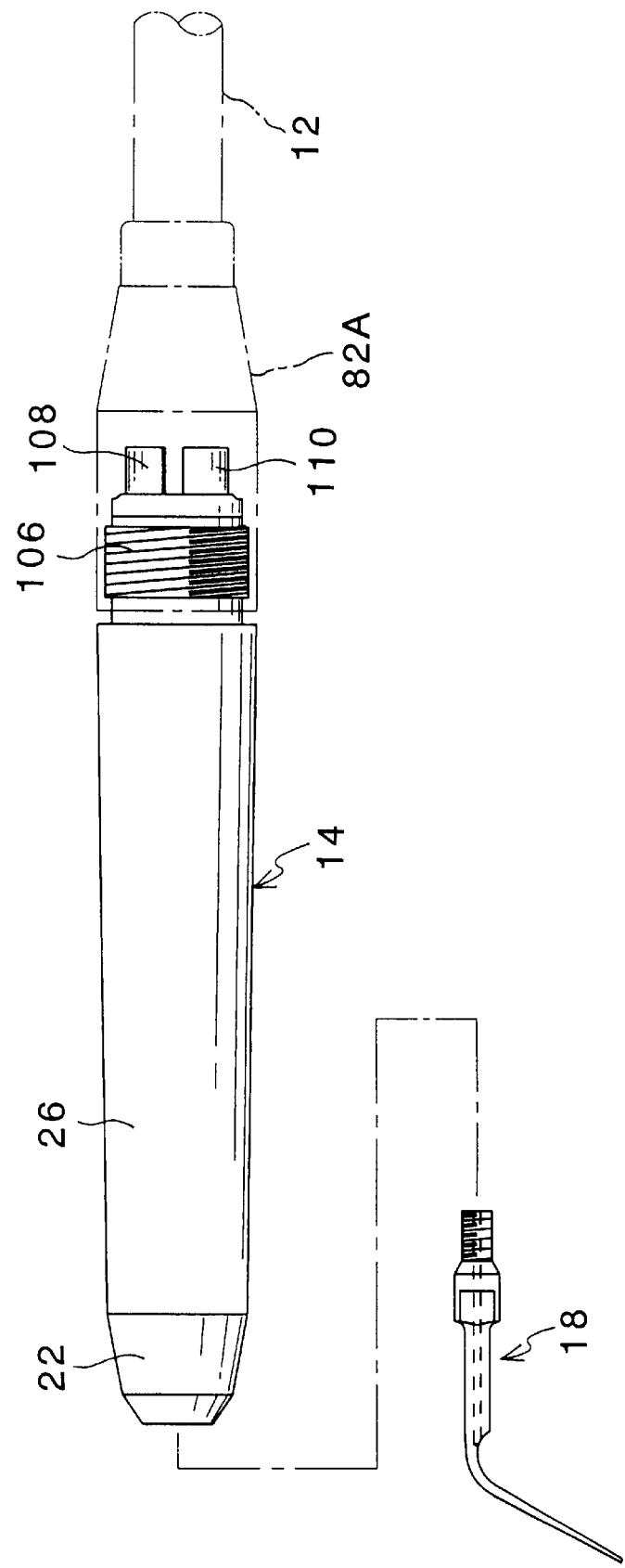
FIGS. 7 and 8 are views similar to FIGS. 1 and 2, respectively, but showing a modified version of the dental scaler.
Figure 8:
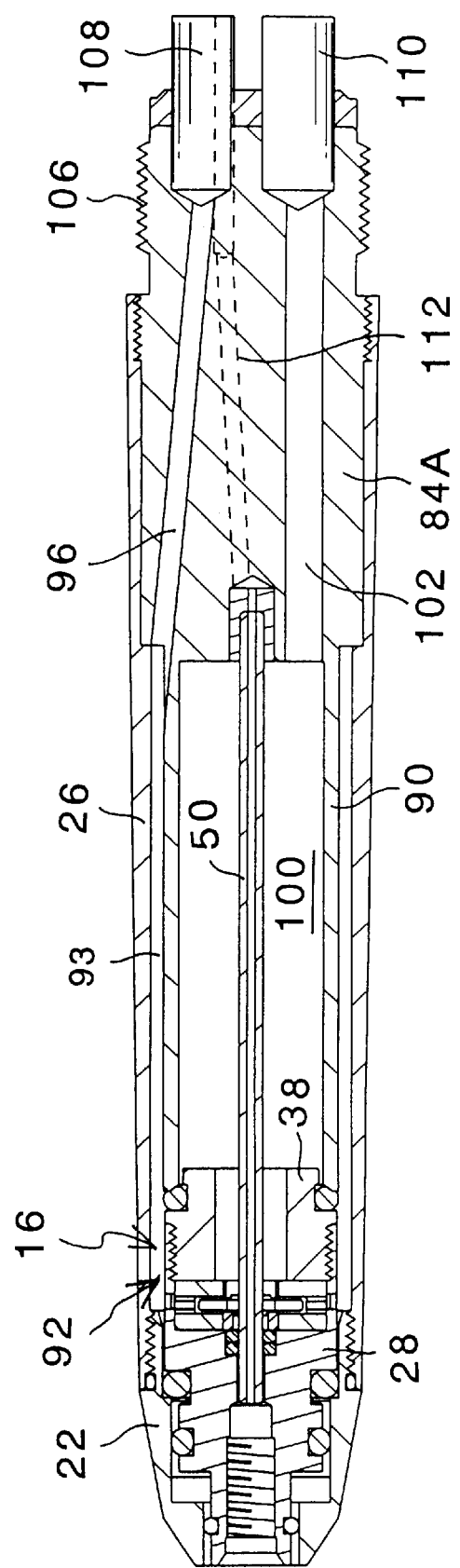

FIGS. 7 and 8 illustrate a modified version of the dental scaler embodying the invention. The modified version differs from the first embodiment only in that a conventional hose coupling of the threaded type is used in place of the ball-lock type quick coupling mechanism employed in the first embodiment. Therefore, parts and members similar to those of the first embodiment are indicated in FIGS. 7 and 8 by like reference numerals and will not be described again.

To describe only the difference with reference to FIGS. 7 and 8, a male coupling member 84A fitted within the main body 26 of the outer casing 14 is provided with external threads 106 which are intended to threadingly engage with internal threads, not shown, provided in a female coupling member 82A of the hose coupling. The female member 82A may be a standardized conventional member of the four hole type, for example.

The male coupling member 84A is provided with a compressed air inlet 108 communicated with the air passage 96, a water passage 112 communicated with the water pipe 50, and a water inlet communicated with the water passage 112, the water inlet being concealed in FIG. 8 by the air inlet 108.

In use, the dental scaler of the modified version is detachably connected to the dental hose 12 by screwing the male member 84A and the female member 82A together. In other respects, the operation of the dental scaler and the manner of replacement of the vibrator module are the same as those described with reference to the first embodiment.

Figure 9:
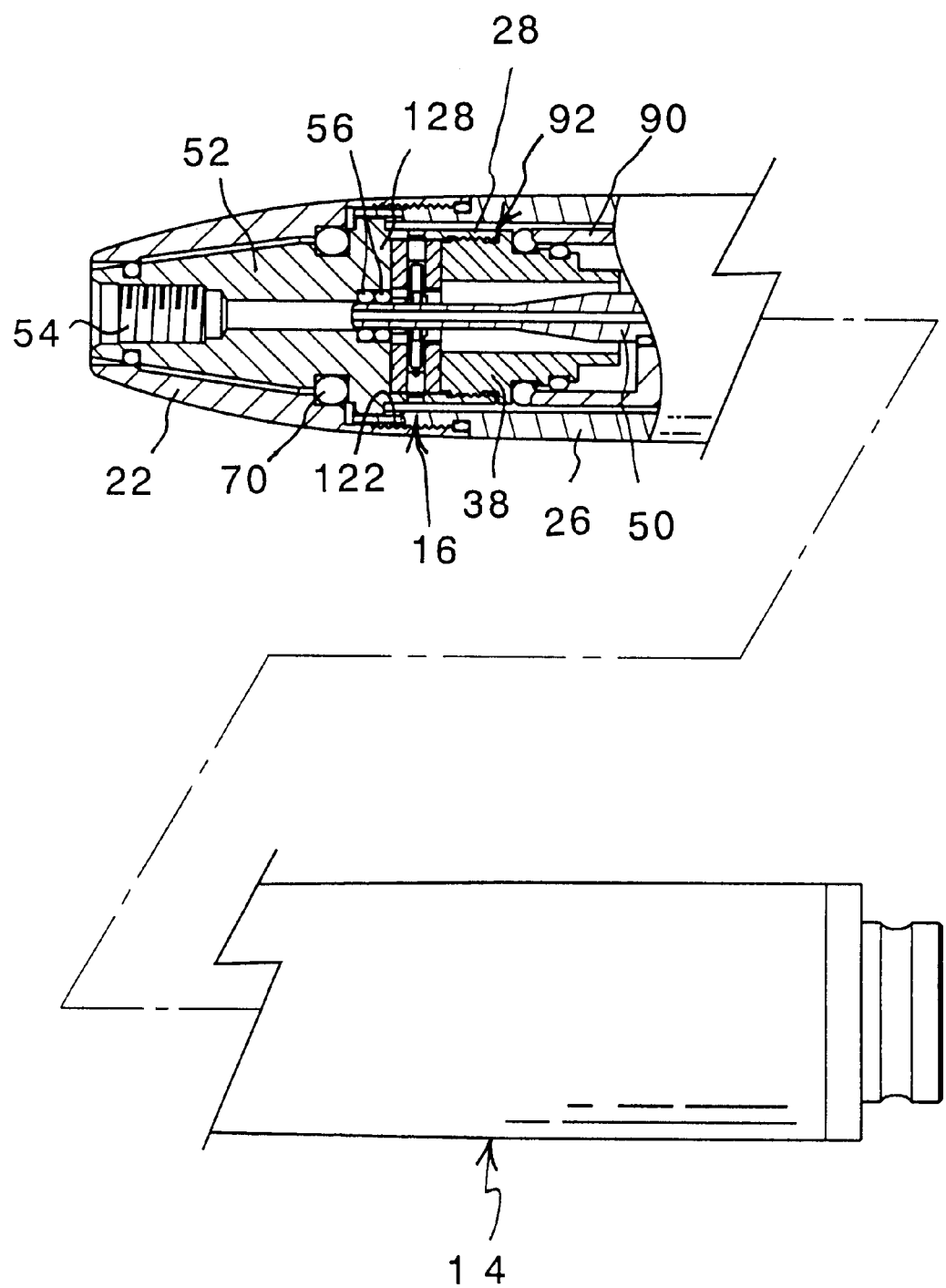
FIG. 9 is an elevational view, partly in cross-section, of the dental scaler according to the third embodiment of the invention.
Figure 10:
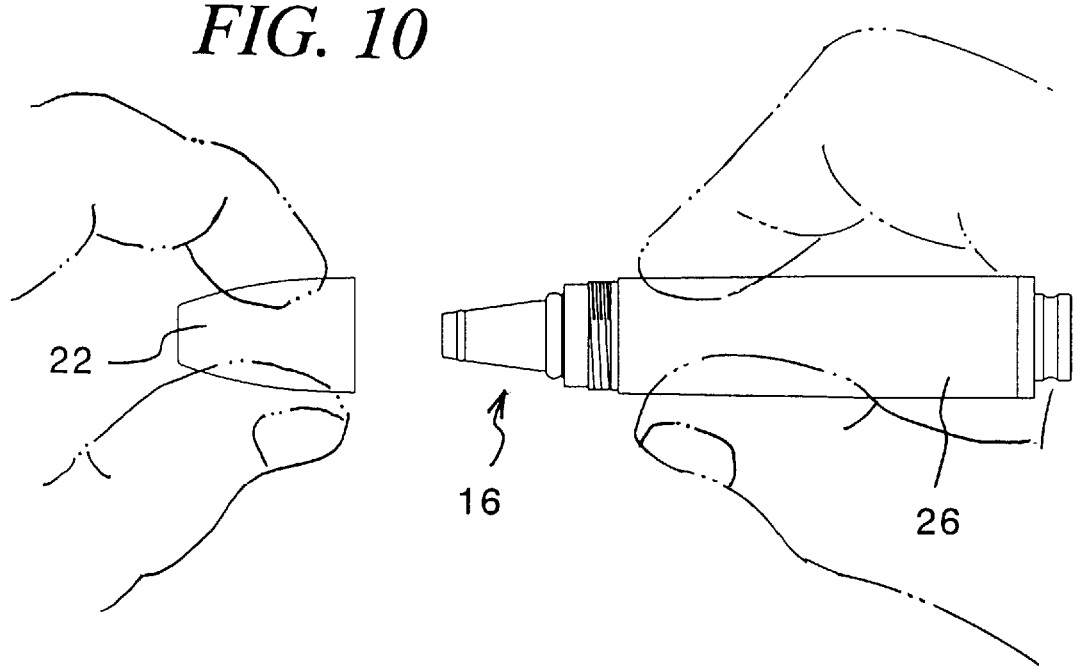
FIG. 10 is an elevational view of the scaler shown in FIG. 9 but showing the frontal cap as disconnected from the main body of the outer casing.
Figure 11:
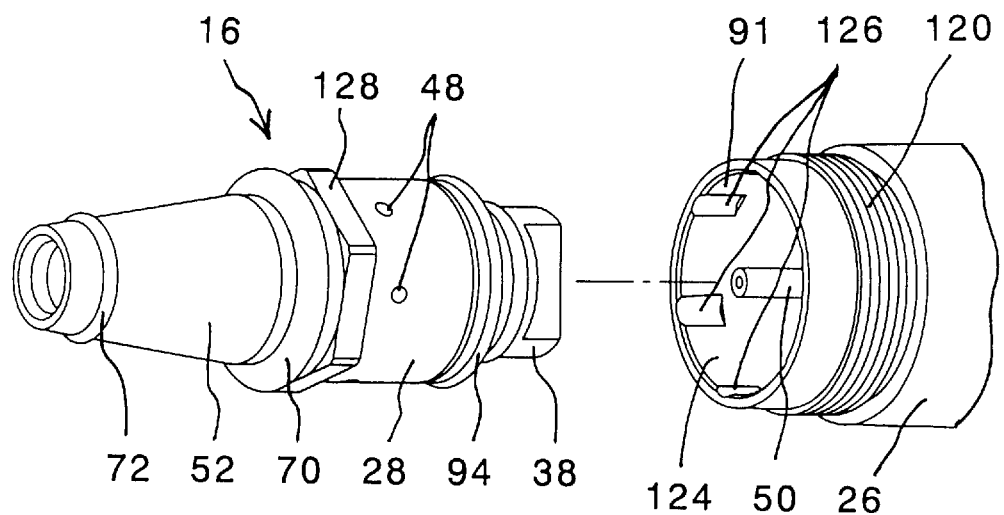
FIG. 11 is a perspective view showing the vibrator module of the scaler shown in FIG. 9 as mounted to and dismounted from the outer casing.
Figure 12:
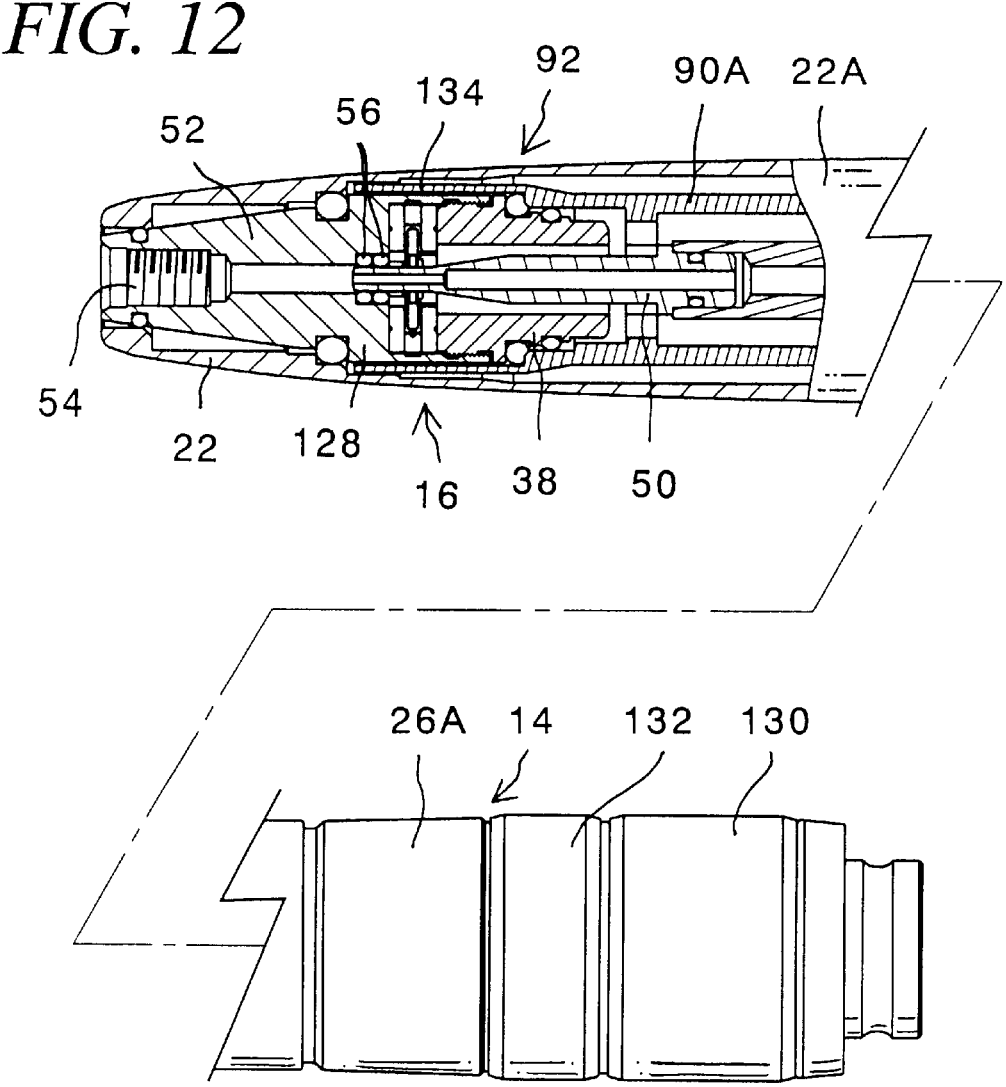
FIG. 12 is a view similar to FIG. 9 but showing the dental scaler according to the fourth embodiment of the invention.

FIGS. 9–11 illustrate the dental scaler according to the third embodiment of the invention. The feature of this embodiment is that the vibrator module 16 is rotationally locked against the main body 26. In FIGS. 9–11, parts and members similar to those of the first embodiment are indicated by like reference numerals and will not be described again.

To describe only the difference, the threaded coupling for detachably coupling the frontal cap 22 and the main body 26 includes an external or male thread 120 formed on the frontal outer periphery of the main body 26 and an internal or female thread 122 formed on the rear inner periphery of the frontal cap 22.

As in this embodiment the coupling thread 120 of the main body 26 is formed externally of the main body 26, the frontal cavity 91 of the main body 26 presents a cylindrical inner periphery 124 which is free from any threading. This permits to provide the inner periphery 124 of the frontal cavity 91 with a plurality of notches or undercuts 126, numbering six for example, which are circumferentially equally spaced apart from each other. These notches 126 may be readily formed, for example, by partly milling or drilling the inner periphery 124 of the cavity 91 in the axial direction.

In conformity with the notches 126 formed on the inner periphery 124 of the main body 26, a locking formation 128 having a hexagonal cross-section is formed between the casing 28 and the shank 52 of the vibrator module 16, the shank 52 in this embodiment being tapered to enhance transmission of acoustic vibration. The cross-sectional dimension of the locking formation 128 is so selected that the dihedral corners of the hexagonal cross-section are loosely engaged within respective notches 126.

To replace the vibrator module 16, the scaling tip 18 is first disconnected from the vibrator module 16 by unscrewing the tip 18 with a wrench while securely holding the main body 26 by one hand. Contrary to the first embodiment, the frontal cap 22 will be exempted from a torque exerted by the wrench as in this embodiment the vibrator module 16 is locked by the anti-rotation arrangement 126/128 against the main body 26. This prevents the frontal cap 22 from being inadvertently loosened when the scaling tip 18 is unscrewed.

Then the cap 22 and the main body 26 are disconnected from each other as shown in FIG. 10 by unscrewing the thread 122 of the cap 22 and the thread 120 of the main body 26 from each other by hands.

As in the third embodiment the vibrator module 16 is rotationally locked against the main body 26 as described before, a static friction will exist at the contact between the water pipe 50 and the O-rings 56 whereas a sliding friction will be developed at the contact between the frontal cap 22 and the O-rings 70 and 72, when the cap 22 and the main body 26 are unscrewed from each other. As a result, when the cap 22 and the main body 26 are separated, the vibrator module 16 will remain attached to the main body 26 as shown in FIG. 10.

Accordingly, by holding the main body 26 by the fingers of the one hand, with the vibrator module 16 held by the fingers of the other hand, and by pulling the main body 26 and the module 16 apart, the vibrator module 16 will be readily separated from the main body 26 as shown in FIG. 11.

When a new vibrator module is to be mounted to the scaler 10, the vibrator module 16 is first angularly positioned by rotating it relative to the main body 26 until the corners of the hexagonal locking formation 128 are fitted respectively within the notches 126, whereupon the module 16 is pushed into the main body 26 partly. It will be understood from FIG. 11 that as the locking formation 128 has a hexagonal cross-section, the vibrator module 16 may be readily fitted onto the main body 26 only by relative rotation of maximum 60 degrees.

Then the cap 22 is screwed onto the main body 26 and the scaling tip 18 is screw coupled to the vibrator module 16 by using a wrench. During screwing of the scaling tip 18, the torque applied by the wrench will be withstood by the main body 26 so that the cap 22 will be exempted from the screwing torque applied by the wrench. This advantageously prevents the cap 22 from being excessively tightened. Therefore, the frontal cap 22 may readily be loosed by hand when desired.

FIGS. 12–15 illustrate the dental scaler according to the fourth embodiment of the invention. Parts and members similar to those of the foregoing embodiments are indicated by like reference numerals and will not be described again. The vibrator module 16 incorporated in this embodiment is identical with that used in the third embodiment shown in FIGS. 9–11.

The feature of this embodiment is that the frontal cap is made considerably longer and slightly more slim as compared with the third embodiment. To this end, the arrangement is such that the vibrator module 16 is rotationally locked against the positioning sleeve.

More specifically, referring to FIGS. 12–15, the frontal cap 22A has an axial length which is greater than a half of the entire axial length of the handpiece 10. The main body 26A of the outer casing is correspondingly shortened. As a result, the juncture between the main body 26A and the frontal cap 22A is located considerably rearwardly of the frontal end of the positioning sleeve 90A.

The handpiece 10 is provided at its rear part with a conventional valve unit 130 for controlling the flow rate of compressed air fed to the vibrator module 16 and another conventional valve unit 132 for controlling the flow rate of cooling and cleaning water supplied to the scaling tip 18. The provision for the valve units 130 and 132 allows the user to adjust the power of the vibrator and the flow rate of cooling water as required. However, these valve units are not indispensable. As these valve units 130 and 132 are conventional and do not form part of the invention, the details thereof need not be shown and described.

The positioning sleeve 90A is integrally connected to a tubular housing 134 which defines the cavity 91 forming part of the lodgment 92 for accommodating the vibrator module 16. As shown, the housing 134 is provided with a plurality of axially extending recesses or cutouts 136 circumferentially spaced apart from each other. The cutouts 136 are designed to cooperate with the respective corners of the hexagonal formation 128 of the vibrator module 16 to rotationally lock the module 16 with respect to the positioning sleeve 90A.

Use of the positioning sleeve 90A for the purpose of anti-rotational locking of the vibrator module enables to make the frontal cap 22A longer and to thereby eliminate the threaded coupling 20/24 and 120/122 of the foregoing embodiments from that region of the handpiece which is located immediately radially outwardly of the vibrator module 16. This permits to reduce as far as possible the outer diameter of the frontal cap at the location at which the user's fingers are engaged during dental treatment. Although the possible reduction in the outer diameter of the frontal cap is as small as in the order of less than about 1 mm, it considerably facilitates the user to snugly grip the handpiece and to precisely position the dental tool with respect to the tooth under treatment.

Figure 15:
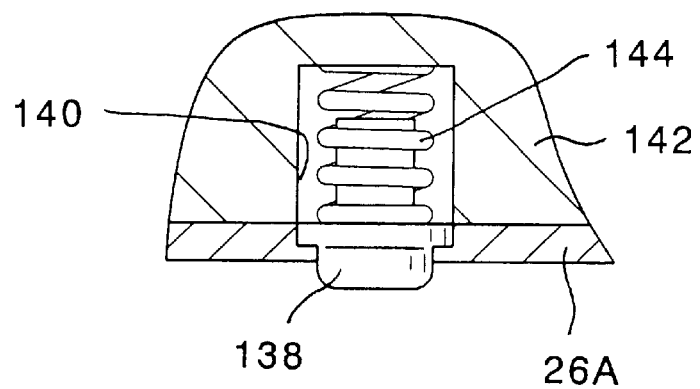
FIG. 15 is an enlarged cross-sectional view taken along the line XV—XV of FIG. 13.

In this embodiment, the frontal cap 22A and the main body 26A are detachably coupled with each other by a quick coupling arrangement, instead of the threaded coupling 120/122 used in the third embodiment. Thus, as shown in FIG. 15, a retractable lock pin 138 is slidably mounted within a radial hole 140 formed in a coupling insert 142 closely fitted within the casing main body 26A. The lock pin 138 is biased radially outwardly by a coil spring 144 for engagement with a through opening 146 formed in the frontal cap 22A.

In use, the frontal cap 22A and the main body 26A are coupled with each other by the locking pin 138 engaged in the associated hole 146. As the vibrator module 16 is rotationally locked against the positioning sleeve 90A by means of the anti-rotation arrangement 128/134/136, a torque applied by a wrench to the scaling tip 18 for screwing and unscrewing it to and from the vibrator module 16 will be transmitted first to the positioning sleeve 90A and will transmitted therefrom to the frontal cap 22A through the lock pin 138. Because the frontal cap 22A is made long enough and is therefore easy to grip, the torque applied by the wrench will be fully resisted by hand by firmly gripping the frontal cap 22A.

Figure 13:
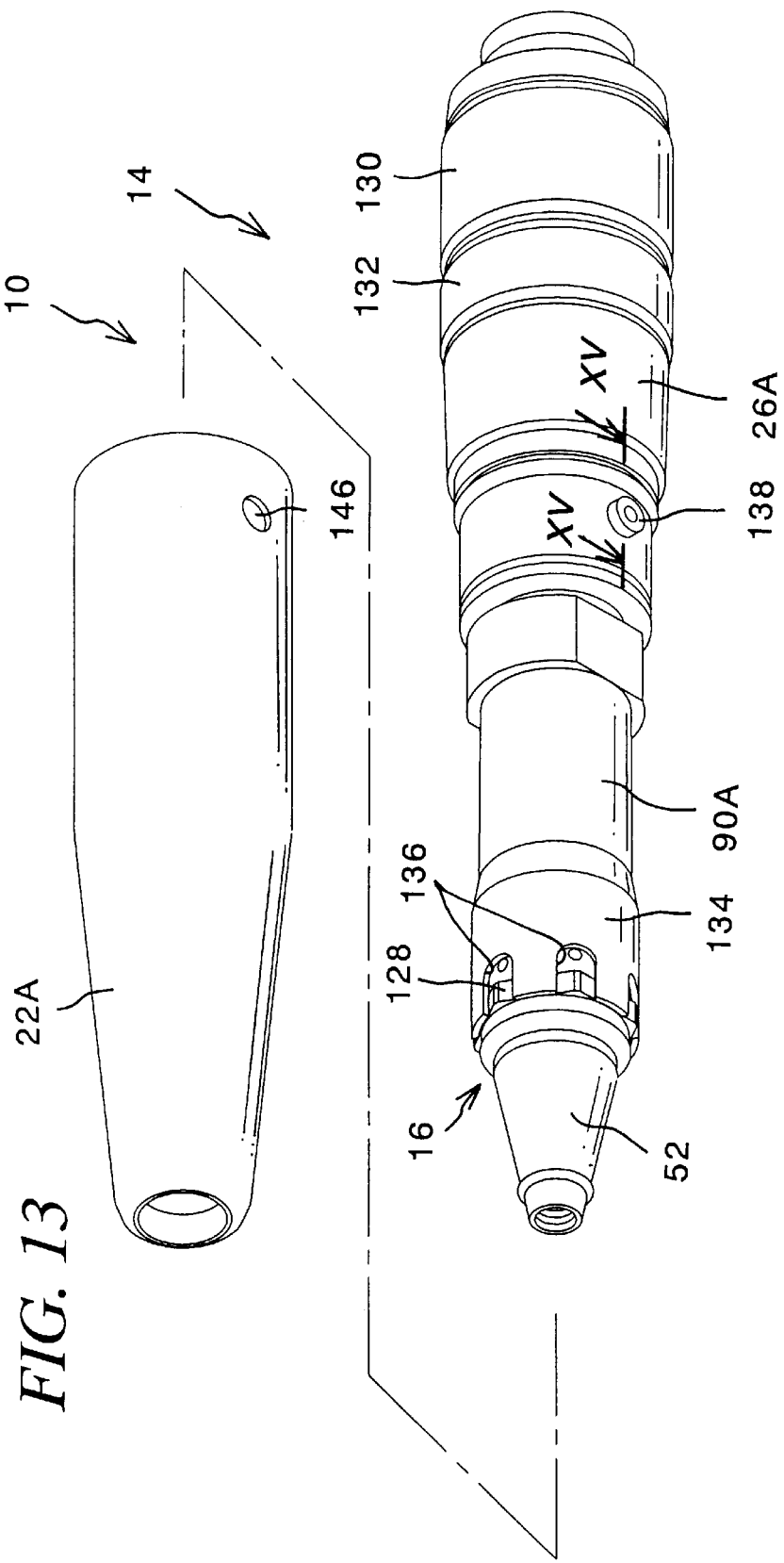
FIG. 13 is a perspective view of the dental scaler shown in FIG. 12 and showing the frontal cap as disconnected from the main body of the outer casing.
Figure 14:
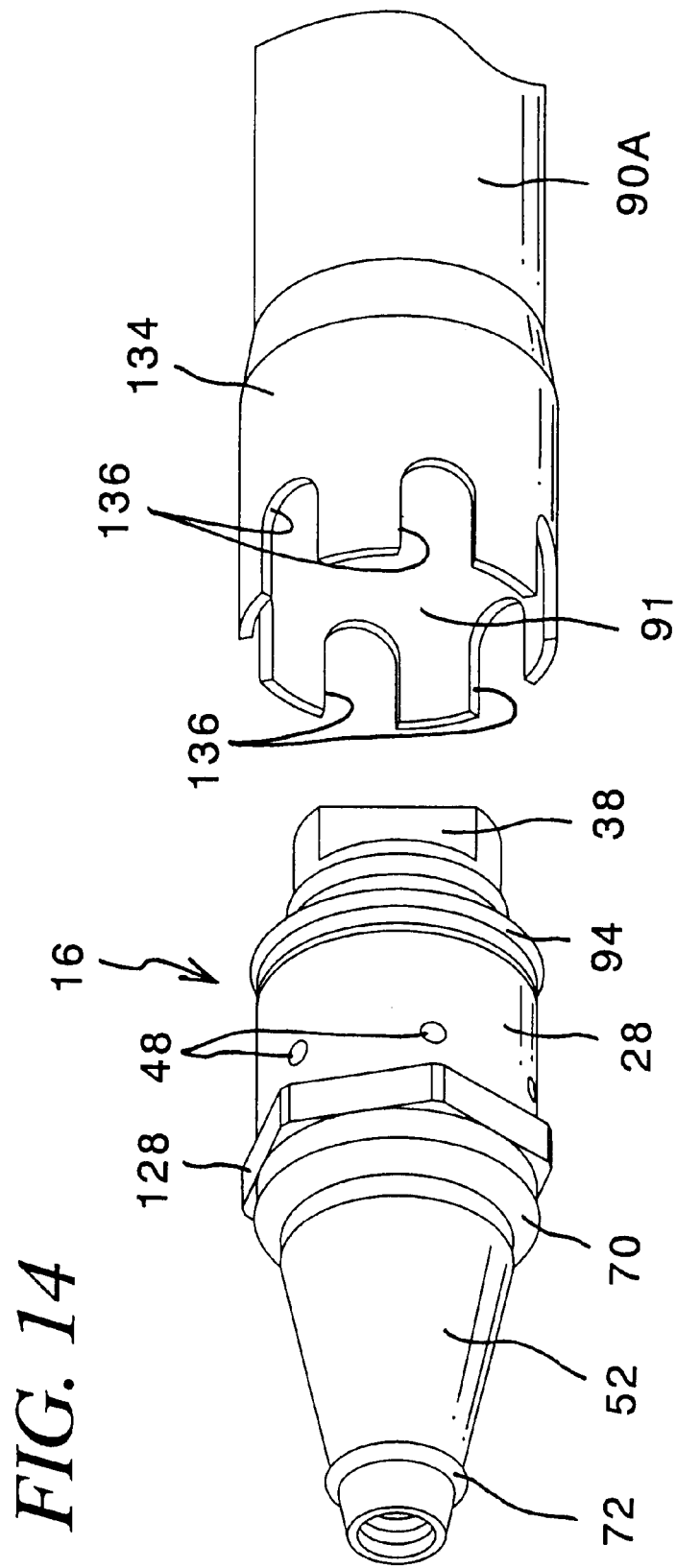
FIG. 14 is a view similar to FIG. 11 but showing the vibrator module of the scaler shown in FIG. 13 as mounted to and dismounted from the outer casing.

For replacement of the vibrator module 16, the scaling tip 18 is first removed from the vibrator module 16 and the lock pin 138 is pushed inwardly to disengage from the hole 146. When the frontal cap 22A is disconnected from the main body 26A, the vibrator module 16 will remain attached to the housing 134 as shown in FIG. 13. It will be noted that it is now easy to grip the module 16 by fingers and replace it with a new one as shown in FIG. 14.

During daily use of the handpiece, it is preferable to dismount the frontal cap 22A from the handpiece and subject only the frontal cap to sterilization by an autoclave and cleansing by a supersonic cleansing device. As the frontal cap covers a substantial length of the handpiece, the handpiece may be kept substantially clean and hygienic by frequently subjecting only the cap to sterilization and cleansing. Sterilization merely of the frontal cap is advantageous in protecting the vibrator module and other parts of the handpiece from thermal degradation so that the service life of these components will be prolonged.

Figure 16:
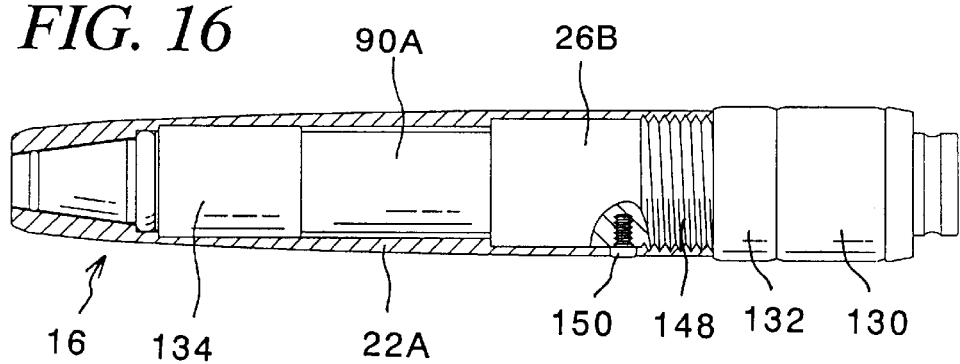
FIG. 16 is an elevational view, partly in cross-section, of the air-driven dental scaler according to a further embodiment of the invention; and, FIG. 17 is an elevational view, partly in cross-section, of the air-driven dental scaler according to another embodiment of the invention.
Figure 17:
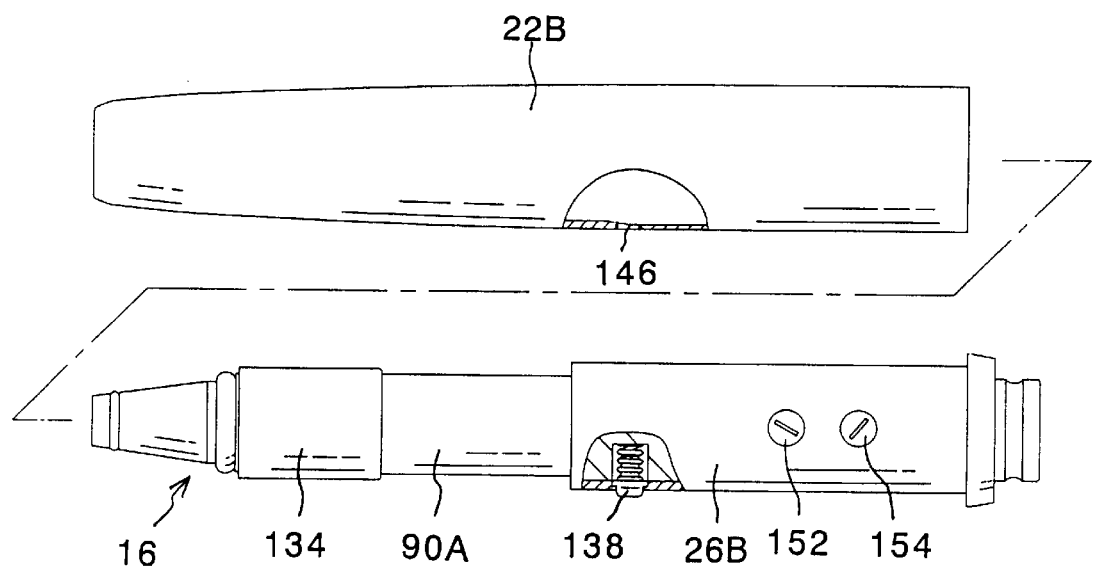

FIGS. 16 and 17 illustrate other embodiments of the invention. Likewise, parts and members similar to those of the foregoing embodiments are indicated by like reference numerals.

In the embodiment shown in FIG. 16, the frontal cap 22A and the main body 26B forming part of the outer casing are detachably coupled with each other by threaded coupling 148 and are locked with each other by a lock screw 150. The lock screw 150 advantageously prevents the cap 22A and the main body 26B from being undesirably loosened as the scaling tip is screwed to the vibrator module 16.

In the embodiment illustrated in FIG. 17, the frontal cap 22B is made long enough to cover substantially the entire length of the handpiece to facilitate sterilization and to improve hand grip as described before. The cap 22B also serves to conceal adjusting screws 152 and 154 of the flow control valves incorporated in the main body 26B to control the flow rate of compressed air and cooling water. Once the adjusting screws 152 and 154 are set and the cap 22B and the main body 26B are coupled with each other by the lock pin 138, the cap 22B will serve to preclude the adjusting screws 152 and 154 from being inadvertently contacted.

While the present invention has been described herein with reference to the specific embodiments thereof, it is contemplated that the present invention is not limited thereby and various changes and modifications may be made therein for those skilled in the art without departing from the scope of the invention. For example, the air-driven dental instrument according to the invention may be used in any desired application other than dental scaling. The structure, form and number of the elements forming the anti-rotation mechanism may be altered. In particular, the hexagonal formation may be changed to triangular, quadrangular or pentagonal formation or may be replaced by one or more pins.

What is claimed is:

1. An air-driven dental vibratory instrument, comprising, an elongated outer casing having a longitudinally extending lodgment defined contiguous to a frontal end of said casing, said casing being split into a main body and a frontal cap said main body and frontal cap opening to the lodgment at mating ends connected with each other at a juncture,
   an air-driven vibrator module having a housing portion having a chamber containing a vibratory element for generating vibration, and a frontal part extending from said housing portion and having threaded coupling means for detachably coupling a vibratory tool, said housing portion being received within the lodgement and removable from the lodgement through an opening at a mating end upon disconnecting said frontal can from the main body at the juncture,
   means for resiliently supporting said module in said casing,
   axial positioning means for locating said vibrator module against said frontal cap,
   means for supplying compressed air to said vibrator module to excite said vibratory element, and,
   anti-rotation means for preventing said vibrator module from rotating relative to said casing when said vibratory tool is screwed to and unscrewed from said vibrator module,
   wherein the axial position of the juncture between said main body and said frontal cap is such that, when said main body and said frontal cap are disconnected from each other for replacement of said vibrator module, at least part of the main housing of said vibrator module is exposed, extending from said main body or frontal cap to which it is attached, to thereby permit an operator to hold said module by fingers in order to remove said module from the lodgement within said main body or frontal cap.

2. A vibratory instrument according to claim 1, wherein said anti-rotation means is operable to lock the vibrator module against the frontal cap so that, when the main body and the frontal cap are disconnected from each other, the vibrator module remains attached to the frontal cap, and wherein an axial length of the frontal cap is smaller than that of the vibrator module to ensure that a rear part of the vibrator module is exposed from the frontal cap as the main body and the frontal cap are disconnected from each other, to thereby permit the operator to grip on said rear part of the module in order to remove the module from the frontal cap.

3. A vibratory instrument according to claim 2, wherein an axial length of the frontal cap is roughly equal to a half of that of the vibrator module to ensure that a rear half of the vibrator module is exposed from the frontal cap for operator's grip as the main body and the frontal cap are disconnected from each other.

4. A vibratory instrument according to claim 1, wherein said anti-rotation means is operable to lock the vibrator module against the main body so that, when the main body and the frontal cap are disconnected from each other, the vibrator module remains attached to the main body, and wherein an axial length of the frontal cap is smaller than that of the vibrator module to ensure that a frontal part of the vibrator module is exposed from the main body as the main body and the frontal cap are disconnected from each other, to thereby permit the operator to grip on said frontal part of the module in order to remove the module from the main body.

5. A vibratory instrument according to claim 4, wherein an axial length of the frontal cap is roughly equal to a half of that of the vibrator module to ensure that a frontal half of the vibrator module is exposed from the main body for operator's grip as the main body and the frontal cap are disconnected from each other.

6. A vibratory instrument according to claim 4, wherein said anti-rotation means operating to lock the vibrator module against the main body is also operable to ensure that a torque applied to said vibratory tool to screw it to or unscrew it from the vibrator module is withstood by the main body whereby the frontal cap is exempt from said torque.

7. A vibratory instrument according to claim 4, wherein said anti-rotation means includes at least one notch formed on the inner periphery of the main body and at least one corresponding projection provided on the outer periphery of the vibrator module for engagement with said notch.

8. A vibratory instrument according to claim 7, wherein said anti-rotation means includes a formation of a polygonal cross-section provided on the outer periphery of the vibrator module.

9. A vibratory instrument according to claim 8, wherein said formation has a hexagonal cross-section.

10. A vibratory instrument according to claim 1, wherein said axial positioning means includes a positioning sleeve extending axially within said casing and secured to said main body, wherein said anti-rotation means is operable to lock the vibrator module against said positioning sleeve so that, when the frontal cap is disconnected from the main body, the vibrator module tends to remain attached to the positioning sleeve, and wherein the juncture between the main body and the frontal cap is located rearwardly of a frontal end of the positioning sleeve to ensure that a frontal part of the vibrator module is exposed from the positioning sleeve as the main body and the frontal cap are disconnected from each other, to thereby permit the operator to grip on said frontal part of the module in order to remove the module from the positioning sleeve to which it is attached.

11. A vibratory instrument according to claim 10, wherein an axial length of the frontal cap is greater than a half of the entire axial length of the outer casing.

12. A vibratory instrument according to claim 11, wherein the frontal cap is long enough to cover substantially the entire length of the instrument.

13. A vibratory instrument according to claim 10, wherein the main body and the frontal cap are detachably joined with each other by threaded coupling.

14. A vibratory instrument according to claim 13, further comprising a lock screw for locking the frontal cap to the main body.

15. A vibratory instrument according to claim 10, wherein the main body and the frontal cap are detachably coupled with each other by a retractable lock pin.

16. A vibratory instrument according to claim 10, wherein said anti-rotation means includes at least one projection provided on the outer periphery of the vibrator module and a retaining element formed integrally with the positioning sleeve to cooperate with said projection.

17. A vibratory instrument according to claim 16, wherein said anti-rotation means includes a formation of a polygonal cross-section formed on the outer periphery of the vibrator module and wherein said retaining element has a plurality of recesses in which dihedral corners of said polygonal formation are engageable respectively.

18. A vibratory instrument according to claim 17, wherein said formation has a hexagonal cross-section.

19. An air-driven dental scaler having a scaling tip mounted to the vibrator module of the vibratory instrument according to one of the preceding claims.

20. A vibratory instrument according to claim 1 wherein the outer diameter of said housing portion of said module is smaller than a diameter of said lodgment at said juncture.

21. A vibratory instrument according to claim 10 wherein the outer diameter of said housing portion of said module is smaller than a diameter of said lodgment at said juncture.

* * * * *